United States Patent [19]

Nishiyama et al.

[11] 4,310,530
[45] Jan. 12, 1982

[54] N-BENZOYL N-PYRIDYLOXY PHENYL UREA

[75] Inventors: Ryuzo Nishiyama, Takatsuki; Takahiro Haga, Kusatsu; Tadaaki Toki; Tohru Koyanagi, both of Moriyama; Shigeo Murai, Yookaichi, all of Japan

[73] Assignee: Ishihara Sangyo Kaisha Ltd., Osaka, Japan

[21] Appl. No.: 183,650

[22] Filed: Sep. 3, 1980

[30] Foreign Application Priority Data

Sep. 7, 1979 [JP] Japan .................. 54-114862
Feb. 8, 1980 [JP] Japan .................. 55-14430

[51] Int. Cl.³ .................. C07D 213/64; A01N 43/40
[52] U.S. Cl. .................. 424/263; 546/291
[58] Field of Search .................. 546/291, 300; 424/263

[56] References Cited

U.S. PATENT DOCUMENTS 4,173,637 11/1979 Nisniyama et al. .................. 546/300
4,173,638 11/1979 Nishiyama et al. .................. 546/300

*Primary Examiner*—Alan L. Rotman

*Attorney, Agent, or Firm*—Oblon, Fisher, Spivak, McClelland & Maier

[57] ABSTRACT

N-benzoyl N'-pyridyloxy phenyl ureas having the formula

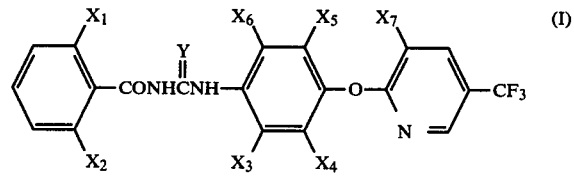

wherein $X_1$ represents a hydrogen or halogen atom or methyl, trifluoromethyl or nitro group; $X_2$ represents a hydrogen or halogen atom; $X_3$, $X_4$, $X_5$ and $X_6$ respectively represent a hydrogen or halogen atom or a $C_1$–$C_4$ alkyl group, a $C_1$–$C_4$ alkoxy group, a $C_1$–$C_4$ alkylcarbonyl group, a $C_1$–$C_4$ alkoxycarbonyl group or nitro group; when $X_3$ and $X_6$ are both hydrogen atoms, at least one of $X_4$ and $X_5$ is a $C_1$–$C_4$ alkyl group, a $C_1$–$C_4$ alkoxy group, a $C_1$–$C_4$ alkylcarbonyl group, or a $C_1$–$C_4$ alkoxycarbonyl group; and $X_7$ represents a hydrogen or halogen atom; and Y represents oxygen or sulfur atom.

9 Claims, No Drawings

N-BENZOYL N-PYRIDYLOXY PHENYL UREA

BACKGROUND OF THE INVENTION

1. Field of the Invention

The present invention relates to novel N-benzoyl N'-pyridyloxy phenyl ureas and the process for producing the same and the insecticidal composition containing the same.

2. Description of the Prior Arts

Almost of the conventional insecticides impart neurotoxicity and contact toxicity to all kinds of insects.

It has been required to find selective insecticidal compounds without toxicity to useful insects, N-benzoyl N'-phenyl ureas disclosed in U.S. Pat. No. 3,748,356 and N-benzoyl N'-pyridyloxy phenyl ureas disclosed in U.S. Pat. Nos. 4,173,637 and 4,173,638 have such insecticidal properties.

The N-benzoyl N'-pyridyloxy phenyl ureas according to the present invention have a substantially better action than the above described known compounds.

SUMMARY OF THE INVENTION

It is an object of the present invention to provide novel N-benzoyl N'-pyridyloxy phenyl ureas.

It is another object of the present invention to provide a process for producing N-benzoyl N'-pyridyloxy phenyl ureas.

It is the other objects of the present invention to provide selective insecticidal compositions which are remarkably effective to certain injurious insects without affecting useful insects in remarkably low toxicity to animals.

The novel compounds of the present invention are N-benzoyl N'-pyridyloxy phenyl ureas having the formula

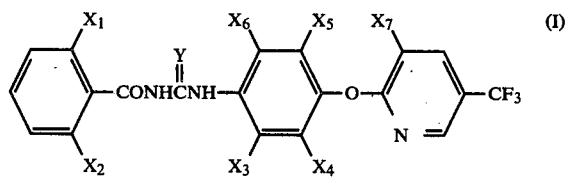

wherein $X_1$ represents a hydrogen or halogen atom or methyl, trifluoromethyl or nitro group; $X_2$ represents a hydrogen or halogen atom; $X_3$, $X_4$, $X_5$ and $X_6$ respectively represent a hydrogen or halogen atom or a $C_1$-$C_4$ alkyl group, a $C_1$-$C_4$ alkoxy group, a $C_1$-$C_4$ alkylcarbonyl group, a $C_1$-$C_4$ alkoxycarbonyl group or nitro group; when $X_3$ and $X_6$ are both hydrogen atoms, at least one of $X_4$ and $X_5$ is a $C_1$-$C_4$ alkyl group, a $C_1$-$C_4$ alkoxy group, a $C_1$-$C_4$ alkylcarbonyl group, or a $C_1$-$C_4$ alkoxycarbonyl group; and $X_7$ represents a hydrogen or halogen atom; and Y represents oxygen or sulfur atom.

DETAILED DESCRIPTION OF THE PREFERRED EMBODIMENTS:

The present invention is to provide novel N-benzoyl N'-pyridyloxy phenyl ureas having the formula

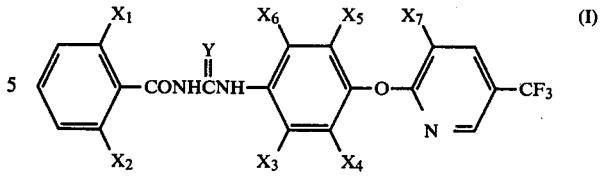

wherein $X_1$ represents a hydrogen or halogen atom or methyl, trifluoromethyl or nitro group; $X_2$ represents a hydrogen or halogen atom; $X_3$, $X_4$, $X_5$ and $X_6$ respectively represent a hydrogen or halogen atom or a $C_1$-$C_4$ alkyl group, a $C_1$-$C_4$ alkoxy group, a $C_1$-$C_4$ alkylcarbonyl group, a $C_1$-$C_4$ alkoxycarbonyl group or nitro group; when $X_3$ and $X_6$ are both hydrogen atoms, at least one of $X_4$ and $X_5$ is a $C_1$-$C_4$ alkyl group, a $C_1$-$C_4$ alkoxy group, a $C_1$-$C_4$ alkylcarbonyl group, or a $C_1$-$C_4$ alkoxycarbonyl group; and $X_7$ represents a hydrogen or halogen atom; and Y represents oxygen or sulfur atom.

In the formula (I), the halogen atom can be fluorine, chlorine, bromine and iodine atom and the lower alkyl group or the alkyl group for the lower alkoxy group can be methyl, ethyl, isopropyl and tert-butyl groups.

The following compounds are typical compounds of the present invention (1) N-benzoyl N'-pyridyloxy phenyl ureas having the formula

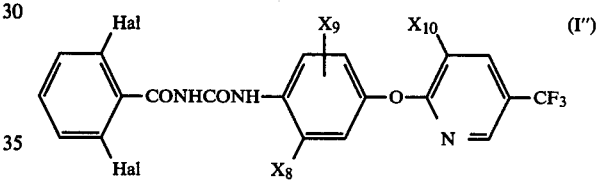

wherein Hal represents a halogen atom; $X_8$ represents a halogen atom, a $C_1$-$C_4$ alkyl group or a $C_1$-$C_4$ alkoxy group; $X_9$ represents hydrogen or halogen atom or a $C_1$-$C_4$ alkyl group; and $X_{10}$ represents a hydrogen or halogen atom and (2) N-benzoyl N'-pyridyloxy phenyl ureas having the formula

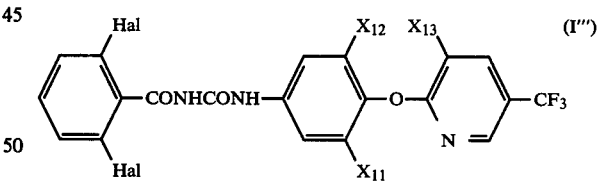

wherein Hal represents a halogen atom; $X_{11}$ represents a $C_1$-$C_4$ alkyl group; $X_{12}$ represents a hydrogen atom or a $C_1$-$C_4$ alkyl group; and $X_{13}$ represents a hydrogen or halogen atom.

The following compounds have excellent insecticidal effects. N-benzoyl N'-pyridyloxy phenyl ureas having the formula

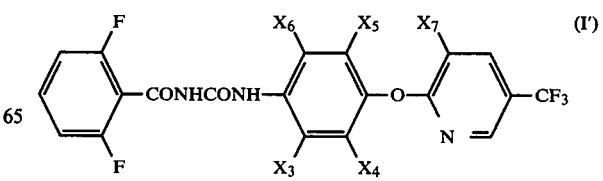

wherein $X_3$, $X_4$, $X_5$ and $X_6$ respectively represent a hydrogen or halogen atom or a $C_1$-$C_4$ alkyl group, a $C_1$-$C_4$ alkoxy group, a $C_1$-$C_4$ alkylcarbonyl group or nitro group and when $X_3$ and $X_6$ are both hydrogen atoms, at least one of $X_4$ and $X_5$ is a $C_1$-$C_4$ alkyl group, and $X_7$ represents a hydrogen or halogen atom. The typical compounds having the formula (I') are as follows. N-2,6-difluorobenzoyl N'-[A-4-(3-halo-5-trifluoromethyl-2-pyridyloxy)-phenyl]ureas wherein A represents 2-chloro, 2,5-dichloro, 2-methyl, 2,5-dimethyl or 3-methyl group.

The N-benzoyl N'-pyridyloxy phenyl ureas having the formula (I) are produced by reacting a compound having the formula

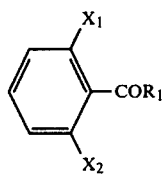
(II)

wherein $X_1$ and $X_2$ are defined above and $R_1$ represents amino or isocyanate or isothiocyanate group with a compound having the formula

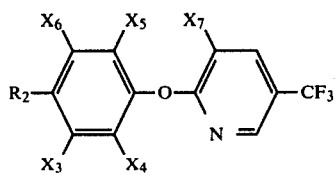
(III)

wherein $X_3$, $X_4$, $X_5$, $X_6$ and $X_7$ are defined above and $R_2$ represents an amino or isocyanate or isothiocyanate group and $R_2$ is amino group in the case that $R_1$ is isocyanate or isothiocyanate group and $R_2$ is isocyanate or isothiocyanate group in the case that $R_1$ is amino group.

More particularly, the compounds having the formula (I) can be produced by the following processes (1) and (2).

(1) The reaction of benzoyl isocyanate having the formula

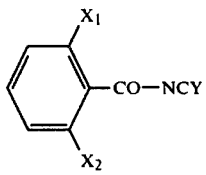
(IV)

($X_1$, $X_2$ and Y are defined above) with pyridyloxy aniline having the formula

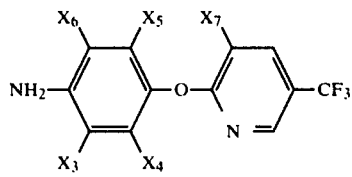
(V)

(wherein in $X_3$, $X_4$, $X_5$, $X_6$ and $X_7$ are defined above) at 0° to 120° C.

(2) The reaction of benzamide having the formula

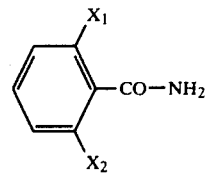
(VI)

($X_1$ and $X_2$ are defined above) with pyridyloxy phenyl isocyanate having the formula

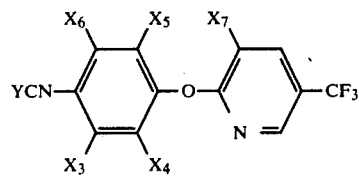
(VII)

(wherein $X_3$, $X_4$, $X_5$, $X_6$ and $X_7$ and Y are defined above) at 50° C. to refluxing temperature.

The reaction is preferably carried out in the presence of a solvent. Suitable solvents include benzene, toluene, xylene, pyridine dioxane, dimethylsulfoxide, monochlorobenzene, ethyl acetate and tetrahydrofuran.

The reaction time is usually in a range of 0.1 to 24 hours. The reaction is preferably carried out at the temperature from 50° C. to a refluxing temperature for 1 to 5 hours.

The aniline compounds having the formula (V)

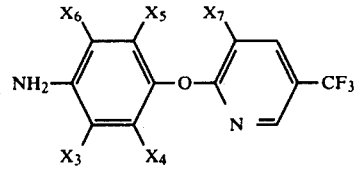

can be produced by reacting a compound having the formula

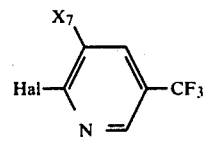

with a compound having the formula

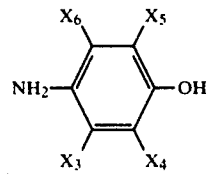

in a solvent in the presence of a base at 70° to 150° C. for 0.5 to 10 hours.

Suitable solvents can be aprotic polar solvents such as dimethylsulfoxide, dimethylformamide and hexamethylphosphoroamide; and ketones such as acetone, methyl ethyl ketone and methyl isobutyl ketone.

Suitable bases can be sodium hydroxide, potassium hydroxide, sodium carbonate and potassium carbonate.

The pyridyloxy phenyl isocyanates having the formula (VII)

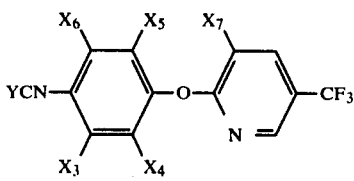

can be produced by reacting a compound having the formula

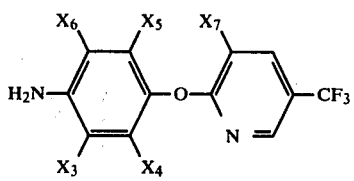

with a compound having the formula

in a solvent at 50° to 150° C. for 0.1 to 24 hours.

Suitable solvents can be solvents inert to phosgene or thiophosgene such as toluene, xylene, monochlorobenzene, ethyl acetate or dioxane.

The condensation reaction is preferably carried out in nitrogen atmosphere.

It is possible to react a 2-halo-5-trifluoromethylpyridine with a phenol in the similar condition to that of the production of the aniline compound to obtain 5-trifluoromethyl-2-pyridylphenyl ether compound and it is converted to the aniline compound by the conventional nitration and a reduction.

Certain examples of preparations of the compounds of the present invention will be described.

EXAMPLE 1

Preparation of
N-2,6-difluorobenzoyl-N'-[2-methyl-4-(3-chloro-5-trifluoromethyl-2-pyridyloxy)phenyl]urea Into a flask, 8.0 g. of 2,3-dichloro-5-trifluoromethylpyridine, 30 ml. of dimethylsulfoxide, 5.0 g. of 3-methyl-4-aminophenol and 6.2 g. of potassium carbonate were charged. Nitrogen gas was fed into flask and the reaction was carried out at 100° to 110° C. for 3 hours. After the reaction, the reaction mixture was cooled and poured into water and an aqueous solution of sodium hydroxide was added. The product was extracted with methylene chloride. The extracted layer was washed with water and dehydrated over anhydrous sodium sulfate and methylene chloride was distilled off to obtain 9.2 g. of 2-amino-5-(3-chloro-5-trifluoromethyl-2-pyridyloxy) toluene having a melting point of 95° to 105° C.

Into the flask, 0.75 g. of 2,6-difluorobenzamide, 20 ml. of 1,2-dichloroethane and 1 g. of oxalylchloride were charged and the mixture was refluxed for 5 hours. After the reaction, the reaction mixture was cooled and 1,2-dichloroethane was distilled off to obtain the oily product. Into the oily product, 20 ml. of anhydrous dioxane was charged, and a solution of 1.5 g. of 2-amino-5-(3-chloro-5-trifluoromethyl-2-pyridyloxy) toluene in 20 ml. of anhydrous dioxane was added dropwise. The reaction was continued at 50° to 60° C. for 1 hours. After the reaction, the reaction mixture was poured into water. The resulting crystal was separated by a filtration, and washed with water and dried to obtain 1.8 g. of N-2,6-difluorobenzoyl-N'-[2-methyl-4-(3-chloro-5-trifluoromethyl-2-pyridyloxy)phenyl]-urea having a melting point of 154° to 161° C.

EXAMPLE 2

Preparation of
N-2,6-difluoro-benzoyl-N'-[2,5-dichloro-4-(3-chloro-5-trifluoromethyl-2-pyridyloxy)phenyl]urea Into a flask, 5.0 g. of 2,3-dichloro-5-trifluoromethylpyridine, 30 ml. of dimethylsulfoxide, 4.2 g. of 2,5-dichlorophenol and 3.6 g. of potassium carbonate were charged, to react them at 110° to 120° C. for 4 hours. After the reaction, the reaction mixture was cooled and charged into water and treated as the process of Example 1 to obtain 7.3 g. of 3-chloro-5-trifluoromethyl-2-pyridyl 2,5-dichlorophenyl ether.

In a flask, 6.4 g. of 3-chloro-5-trifluoromethyl-2-pyridyl 2,5-dichlorophenyl ether and 10 ml. of conc. sulfuric acid were charged in cooling and then, 0.92 ml. of conc. nitric acid was added dropwise at 30° to 40° C. to react them. After the reaction, the reaction mixture was charged into ice water and the product was extracted with methylene chloride. The extracted layer was washed with water, with sodium bicarbonate and with water and dehydrated over anhydrous sodium sulfate. Methylene chloride was distilled off under a reduced pressure to obtain 5.3 g. of 3-chloro-5-trifluoromethyl-2-pyridyl 2,5-dichloro-4-nitrophenyl ether.

In a flask, 3.7 g. of 3-chloro-5-trifluoromethyl-2-pyridyl-2,5-dichloro-4-nitrophenyl ether, 80 ml. of ethanol, 7 ml. of conc. hydrochloric acid and 6.9 g. of stannous chloride were charged, and the mixture was refluxed for 3 hours. After the reaction, the reaction mixture was cooled and poured into water and a conc. aqueous solution of sodium hydroxide was added to it to be strong alkaline solution. The product was extracted with methylene chloride. The extracted layer was washed with water and dehydrated over anhydrous sodium sulfate. Methylene chloride was distilled off under a reduced pressure to obtain 3.4 g. of 3-chloro-5-trifluoromethyl-2-pyridyl 2,5-dichloro-4-aminophenyl ether having a melting point of 105° to 108° C.

In accordance with the process of Example 1 except varying amount of 2,6-difluorobenzamide from 0.75 g. to 0.66 g.; and varying 1.5 g. of 2-amino-5-(3-chloro-5-trifluoromethyl-2-pyridyloxy)toluene to 1.5 g. of 3-chloro-5-trifluoromethyl-2-pyridyl, 2,5-dichloro-4-aminophenyl ether, the reaction and treatment were carried out to obtain 1.8 g. of N-2,6-difluorobenzoyl-[2,5-dichloro-4-(3-chloro-5-trifluoromethyl-2-pyridyloxy)phenyl]urea having a melting point of 190° to 205° C.

EXAMPLE 3

Preparation of
N-2,6-difluorobenzyl-N'-[3-methyl-4-(3-chloro-5-trifluoromethyl-2-pyridyloxy)phenyl]urea Into a flask, 8.0 g. of 2,3-dichloro-5-trifluoromethyl pyridine, 30 ml. of dimethylsulfoxide, 4.8 g. of 2-methyl-4-aminophenol and 5.8 g. of potassium carbonate were charged. Nitrogen gas was fed into the flask and the reaction was carried out at 100°–110° C. for 3 hours. After the reaction, the reaction mixture was cooled and poured into water and an aqueous solution of sodium hydroxide was added. The product was extracted with methylene chloride. The extracted layer was washed with water and dehydrated over anhydrous sodium sulfate and methylene chloride was distilled off to obtain 8.5 g. of 5-amino-2-(3-chloro-5-trifluoromethyl-2-pyridyloxy)toluene.

Into a flask, 0.75 g. of 2,6-difluorobenzamide, 20 ml. of 1,2-dichloroethane and 1 g. of oxalylchloride were charged. The mixture was refluxed for 5 hours. After the reaction, the reaction mixture was cooled and 1,2-dichloroethane was distilled off to obtain an oily product and 20 ml. of anhydrous dioxane was charged, and a solution of 1.3 g. of 5-amino-2-(3-chloro-5-trifluoromethyl-2-pyridyloxy)toluene in 20 ml. of anhydrous dioxane was added dropwise. The reaction was continued at 50° to 60° C. for 1 hour. After the reaction, the reaction mixture was poured into water. The resulting crystal was separated by a filtration and washed with water and dried to obtain 1.8 g. of N-2,6-difluorobenzoyl-N'-[3-methyl-4-(3-chloro-5-trifluoromethyl-2-pyridyloxy)phenyl]urea having a melting point of 162° to 164° C.

EXAMPLE 4

Preparation of N-2,6-difluorobenzoyl-N'-[3-isopropyl-4-(3-chloro-5-trifluoromethyl-2-pyridyloxy)phenyl]urea Into a flask, 16 g. of 2,3-dichloro-5-trifluoromethyl pyridine, 50 ml. of dimethylsulfoxide, 12.2 g. of 2-isopropylphenol and 6.2 g. of potassium carbonate were charged. The mixture was refluxed for 4 hours with stirring. After the reaction, the reaction mixture was cooled and charged into water and an aqueous solution of sodium hydroxide was added. The product was extracted with methylene chloride. The extracted layer was washed with water and dehydrated over anhydrous sodium sulfate and methylene chloride was distilled off to obtain 23.7 g. of 3-chloro-5-trifluoromethyl-2-pyridyl 2-isopropylphenyl ether.

Into a flask, 21.6 g. of 3-chloro-5-trifluoromethylpyridyl 2-isopropylphenyl ether was charged and 10 ml. of conc. sulfuric acid was added dropwise in cooling and then, 3.6 ml. of conc. nitric acid was added dropwise at −20° to −10° C. The reaction was carried out at the ambient temperature for 5 hours with stirring. After the reaction, the reaction mixture was charged into ice water and the product was extracted with methylene chloride. The extracted layer was washed with water, with sodium bicarbonate and with water and dehydrated over anhydrous sodium sulfate. Methylene chloride was distilled off to obtain an oily product. The oily product was purified by a column chromatography to obtain 5.5 g. of 3-chloro-5-trifluoromethyl-2 pyridyl-2-isopropyl-4-nitrophenyl ether.

Into a flask, 5.0 g. of 3-chloro-5-trifluoromethyl-2-pyridyl 2-isopropyl-4-nitrophenyl ether, 25 ml. of ethanol, 10 ml. of conc. hydrochloric acid and 10.3 g. of stannic chloride were charged. The mixture was gradually heated and refluxed for 3 hours with stirring. After the reaction, the reaction mixture was cooled and charged into water and an aqueous solution of sodium hydroxide was added to be an alkaline solution. The product was extracted with methylene chloride. The extracted layer was washed with water and dried and methylene chloride was distilled off to obtain 4.5 g. of 3-chloro-5-trifluoromethyl-2-pyridyl 2-isopropyl-4-aminophenyl ether.

Into a flask, 367 mg. of 2,6-difluorobenzamide, 5 ml. of 1,2-dichloroethane and 1 g. of oxalylchloride were charged and the mixture was refluxed for 5 hours to react them. After the reaction, the reaction mixture was cooled and 1,2-dichloroethane was distilled off to obtain an oily product. In the oily product, 10 ml. of dehydrated dioxane was charged and a solution of 700 mg. of 3-chloro-5-trifluoromethyl-2-pyridyl 2-isopropyl-4-aminophenyl ether in 5 ml. of anhydrous dioxane was added dropwise and the reaction was continued at 50° to 60° C. for 1 hour. The reaction mixture was charged into water. The resulting crystal was separated by a filtration and washed with water and dried to obtain 1.0 g. of N-2,6-difluorobenzoyl-N'-[3-isopropyl-4-(3-chloro-5-trifluoromethyl-2-pyridyloxy)phenyl]urea having a melting point of 145° to 148° C.

EXAMPLE 5

Preparation of N-(2,6-difluorobenzyl)-N'-[2-methyl-4-(3-chloro-5-trifluoromethyl-2-pyridyloxy)phenyl]urea Into a flask, 75 ml. of toluene was charged and dried phosgene gas was fed to saturate it. A solution of 8.4 g. of 2-methyl-4-(3-chloro-5-trifluoromethyl-2-pyridyloxy)aniline in 75 ml. of toluene was added dropwise under feeding phosigne to be slight excess of phosgene in the system at 80° C. After the addition, phosgene was further fed for 10 minutes, and then, excess phosgene was distilled off by heating it to obtain a stoichimetrical amount of 2-methyl-4-(3-chloro-5-trifluoromethyl-2-pyridyloxy)phenylisocyanate. A solution of 4.4 g. of 2,6-difluoro-benzamide in 30 ml. toluene was added and the mixture was refluxed at 110° C. for 20 hours to react them. The reaction mixture was charged into 200 ml. of water and the product was extracted with 100 ml. of ethyl acetate, and the organic layer was dehydrated over anhydrous sodium sulfate and the solvent was distilled off and washed with a small amount of toluene to obtain 12.5 g. of N-(2,6-difluorobenzoyl)-N''-[2-methyl-4-(3-chloro-5-trifluoromethyl-2-pyridyloxy)-phenyl]urea having a melting point of 154°–161° C.

The following typical compounds of the present invention were prepared by one of the processes of Examples 1 to 5 except using the corresponding starting materials. Typical compounds of the present invention having the formula I are as follows.

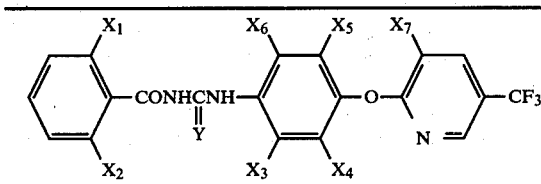

| Exp. No. | $X_1$ | $X_2$ | Y | $X_3$–$X_6$ | $X_7$ | Physical property (melting point) |
|---|---|---|---|---|---|---|
| 1 | Cl | Cl | O | 2-$CH_3$ | Cl | 90–95° C. |
| 2 | F | F | " | " | H | 165–171° C. |
| 3 | " | " | " | " | Cl | 154–161° C. |
| 4 | " | " | " | " | Br | 105–112° C. |
| 5 | " | " | " | 2,5-$(CH_3)_2$ | Cl | 185–189° C. |
| 6 | " | " | " | 2,6-$(CH_3)_2$ | " | 193–197° C. |
| 7 | " | " | " | 2,3,5,6-$(CH_3)_4$ | " | |
| 8 | " | " | " | 2-$CH_3$—5-Cl | " | 170–177° C. |
| 9 | " | " | " | 2-Cl | " | 75–79° C. |
| 10 | " | " | " | 2,3,5-$Cl_3$ | " | 140–148° C. |

-continued

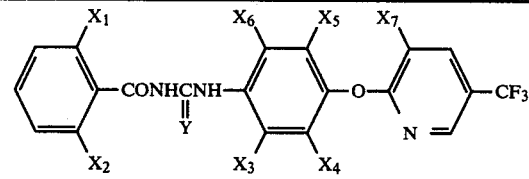

| Exp. No. | $X_1$ | $X_2$ | Y | $X_3$-$X_6$ | $X_7$ | Physical property (melting point) |
|---|---|---|---|---|---|---|
| 11 | " | " | " | 2,6-$Cl_2$ | H | 240–250° C. |
| 12 | " | " | " | 2,5-$Cl_2$ | Cl | 190–205° C. |
| 13 | " | " | " | 2-$CH_3O$ | " | 135–144° C. |
| 14 | Cl | H | " | 2,5-$Cl_2$ | " | 180–193° C. |
| 15 | " | " | " | 2-Cl | " | 145–149° C. |
| 16 | " | " | " | 2,3,5-$Cl_3$ | " | 170–178° C. |
| 17 | " | " | " | 2-$CH_3$ | H | 145–156° C. |
| 18 | " | " | " | " | Cl | 160–165° C. |
| 19 | " | " | S | " | " | 115–128° C. |
| 20 | " | " | O | " | Br | 178–181° C. |
| 21 | " | " | " | 2,5-$(CH_3)_2$ | Cl | 190–194° C. |
| 22 | " | " | " | 2,3,5,6-$(CH_3)_4$ | " | |
| 23 | Br | " | " | 2-$CH_3$ | " | 156–164° C. |
| 24 | F | " | " | " | " | 140–146° C. |
| 25 | $CF_3$ | " | " | " | " | 157–166° C. |
| 26 | $NO_2$ | " | " | " | " | 89–100° C. |
| 27 | H | " | " | " | " | 190–202° C. |
| 28 | " | " | S | " | " | 80–85° C. |
| 29 | $CH_3$ | " | O | " | " | 184–197° C. |
| 30 | " | " | S | " | " | 105–111° C. |
| 31 | F | F | O | 3-$CH_3$ | " | 162–164° C. |
| 32 | Cl | H | " | " | " | 177–180° C. |
| 33 | $CH_3$ | " | " | " | " | 165–166° C. |
| 34 | $NO_2$ | " | " | " | " | 200–202° C. |
| 35 | F | F | " | " | Br | 176–177° C. |
| 36 | Cl | H | " | " | " | 174–176° C. |
| 37 | $CH_3$ | " | " | " | " | 204–206° C. |
| 38 | $NO_2$ | " | " | " | " | 213–216° C. |
| 39 | Br | " | " | " | " | 190–193° C. |
| 40 | H | " | " | 3,5-$(CH_3)_2$ | H | white crystal |
| 41 | Cl | Cl | " | 3-Et | F | " |
| 42 | F | F | " | 3-iso Pr. | Cl | 145–148° C. |
| 43 | Cl | H | " | " | " | 70–72° C. |
| 44 | $CH_3$ | " | O | 3-iso Pr. | Cl | 57–60° C. |
| 45 | $NO_2$ | " | " | " | " | 88–90° C. |
| 46 | Br | " | " | " | " | 71–74° C. |
| 47 | $CF_3$ | " | " | 3-Me | " | 197–199° C. |
| 48 | " | " | " | " | Br | 212–214° C. |
| 49 | H | H | " | " | Cl | 210–212° C. |
| 50 | " | " | " | " | Br | 222–224° C. |
| 51 | F | F | " | 2-$NO_2$ | Cl | 197–202° C. |
| 52 | " | " | " | 3-$COCH_3$ | " | 181–184° C. |
| 53 | " | " | " | 3-COO Et | H | 185–188° C. |

The compounds of the present invention impart excellent selective insecticidal effect as clearly understood from the following experiments.

The compounds of the present invention impart remarkable insecticidal effect to larvae of Lepidoptera, Coleoptera, Hymenoptera and Diptera, for example, larvae of the following insects:

diamondback moth (*Plutella xylostella*), common white (*Pieris rapae crucivora*), cabbage armyworm (*Mamesta brassicae*), cabbage looper (*Plusia nigrisigma*), tobacco cutworm (*Spodoptera litura*), smaller citrus dog (*Papilio xuthus*), small blackish cochlid (*Seopelodes contracta*), fall webworm (*Hyphantria cunea*), gypsy moth (*Lymantria dispar*), rice stem borer (*Chilo suppressalis*), bollworm (*Heliothis zea*), tobacco budworm (*Heliothis virescens*), bollweevil (*Anthonomus grandis*), confused flour beetle (*Tribolium confusum*), colorado potato beetle (*Leptinotarsa decemlineata*), sawfly (Neurotoma irdescens), Culex mosquito (*Culex pipiens pallens*), mosquito (*Culex pipens molestus*).

The compounds of the present invention impart low toxicity to animals.

When the compounds are used as active ingredients of the insecticidal composition, it is possible to prepare various forms of the compositions such as dust, wettable powder, emulsifiable concentrate, invert emulsion, oil solution, aerosol preparation, etc. with adjuvants as the cases of agricultural compositions. The compositions can be applied with or without diluting them in suitable concentrations.

The insecticidal composition is usually formulated by combining 0.5 to 80 wt. % preferably 10 to 50 wt. % of an active ingredient; 5 to 99.5 wt. % preferably 35 to 85 wt. % of a diluent; and 0 to 20 wt. % preferably 5 to 15 wt. % of the other adjuvant.

Suitable adjuvants include powdery carriers such as talc, kaolin, bentonite, diatomaceous earth, silicon dioxide, clay and starch; liquid diluents such as water, xylene, toluene, dimethylsulfoxide, dimethyl formamide, acetonitrile, and alcohol; emulsifiers, dispersing agents, spreaders etc.

The concentration of the active ingredient in the selective insecticidal composition is usually 5 to 80 wt. % in the case of the oily concentrate; and 0.5 to 30 wt. % in the case of dust; 5 to 60 wt. % in the case of wettable powder or an emulsifiable concentrate.

It is also possible to combine with the other agricultural ingredients such as the other insecticides, miticides, plant growth regulators. Sometimes synergetic effects are found.

The selective insecticides of the present invention are effective for inhibiting various injurious insects and they are usually applied at a concentration of the active ingredients of 1 to 10,000 ppm preferably 20 to 2,000 ppm.

It is possible to prevent incubation and growth of notorious insects on excrement by feeding a feed incorporating the active ingredient of the invention.

It is possible to prevent notorious insects live in water by applying the active ingredient of the present invention at said concentration and accordingly, the concentration in water can be lower than said range in water.

Experiment 1

Each active ingredient was dispersed in water to prepare dispersions a concentration of 400 ppm. Leaves of cabbage were dipped into the dispersions for about 10 seconds and taken out and dried under passing air.

A piece of moistened filter paper was put on each Petri dish (diameter 9 cm) and the dried leaves of cabbage were put on the filter paper and larvae of diamondback moth in 2nd or 3rd instar were fed on them and the Petri dishes were covered and kept in constant temperature at 28° C. with lightening. After 8 days from the treatment with the dispersion, the mortal larvae were measured and the mortality rates were calculated by the following equation:

$$\text{Mortality rate} = \frac{\text{Mortal larvae}}{\text{total larvae}} \times 100$$

TABLE 2-1

| Active ingredient | | Mortality rate (%) | Active ingredient | | Mortality rate (%) |
|---|---|---|---|---|---|
| Comp. | 1 | 100 | Comp. | 15 | 100 |
| | 2 | 100 | | 16 | 100 |
| | 3 | 100 | | 17 | 100 |
| | 4 | 100 | | 18 | 100 |

TABLE 2-1-continued

| Active ingredient | Mortality rate (%) | Active ingredient | Mortality rate (%) |
|---|---|---|---|
| 5 | 100 | 19 | 100 |
| 6 | 100 | 20 | 100 |
| 7 | 100 | 21 | 100 |
| 8 | 100 | 22 | 100 |
| 9 | 100 | 23 | 100 |
| 10 | 100 | 24 | 100 |
| 11 | 100 | 26 | 100 |
| 12 | 100 | 29 | 100 |
| 13 | 100 | 30 | 100 |
| 14 | 100 | | |

TABLE 2-2

| Active ingredient | Mortality rate (%) | Active ingredient | Mortality rate (%) |
|---|---|---|---|
| Comp. 31 | 100 | Comp. 41 | 100 |
| 32 | 100 | 42 | 100 |
| 33 | 100 | 43 | 100 |
| 34 | 100 | 44 | 100 |
| 35 | 100 | 45 | 100 |
| 36 | 100 | 46 | 100 |
| 37 | 100 | 47 | 100 |
| 38 | 100 | 48 | 100 |
| 39 | 100 | 49 | 100 |
| 40 | 100 | 50 | 100 |

Experiment 2

In accordance with the method of Experiment 1 except varying the concentration of each active ingredient, the tests were carried out. The results are shown in Table 3.

TABLE 3-1

| Active ingredient | Mortality rate (%) | | |
|---|---|---|---|
| | 200 ppm | 100 ppm | 50 ppm |
| Comp. 31 | 100 | 100 | 100 |
| 32 | 100 | 100 | 100 |
| 33 | 100 | 100 | 100 |
| 34 | 100 | 100 | 100 |
| 35 | 100 | 100 | 100 |
| 36 | 100 | 100 | 100 |
| 37 | 100 | 100 | 100 |
| 38 | 100 | 100 | 100 |
| 39 | 100 | 100 | 100 |
| 40 | 100 | 100 | 100 |
| 41 | 100 | 100 | 100 |
| 42 | 100 | 100 | 100 |

Experiment 3

In accordance with the method of Experiment 1 except using tobacco cutworm (Spodoptera litura) in 2nd or 3rd instar instead of diamondback moth in 2nd or 3rd instar, the tests were carried out. The results are shown in Table 4.

TABLE 4-1

| Active ingredient | Mortality rate (%) | Active ingredient | Mortality rate (%) |
|---|---|---|---|
| Comp. 2 | 100 | Comp. 12 | 100 |
| 3 | 100 | 18 | 100 |
| 4 | 100 | 20 | 100 |
| 9 | 100 | | |

TABLE 4-2

| Active ingredient | Mortality rate (%) | Active ingredient | Mortality rate (%) |
|---|---|---|---|
| Comp. 31 | 100 | Comp. 41 | 100 |

TABLE 4-2-continued

| Active ingredient | Mortality rate (%) | Active ingredient | Mortality rate (%) |
|---|---|---|---|
| 32 | 100 | 42 | 100 |
| 33 | 100 | 43 | 100 |
| 34 | 100 | 44 | 100 |
| 35 | 100 | 45 | 100 |
| 36 | 100 | 46 | 100 |
| 37 | 100 | 47 | 100 |
| 38 | 100 | 48 | 100 |
| 39 | 100 | 49 | 100 |
| 40 | 100 | 50 | 100 |

TABLE 4-3

| Active ingredient | Mortality rate (%) | Active ingredient | Mortality rate (%) |
|---|---|---|---|
| Comp. 51 | 100 | Comp. 53 | 100 |
| 52 | 100 | | |

Experiment 4

Each composition of powdery feed (manufactured by Oriental Enzyme Co.), wheat bran and a solution of each active ingredient at a specific concentration at a ratios of 1:1:2 by weight as a medium for larvae of housefly was put into each cup. Houseflies in 2nd or 3rd instar were put in the cup and the cup was covered with gauze. After 12 days, mortal larvae were measured and the mortality rates were calculated by the equation of Experiment 1. The results are shown in Table 5.

TABLE 5-1

| Active ingredient | Mortality rate (%) | | |
|---|---|---|---|
| | 10 ppm | 5 ppm | 2.5 ppm |
| Comp. 3 | 100 | 100 | 100 |
| 9 | 100 | 90 | 80 |
| 12 | 100 | 100 | 100 |
| 14 | 100 | 100 | 70 |
| 18 | 100 | 100 | 70 |

TABLE 5-2

| Active ingredient | Mortality rate (%) | |
|---|---|---|
| | 80 ppm | 40 ppm |
| Comp. 31 | 100 | 100 |
| 32 | 100 | 100 |
| 35 | 100 | 100 |
| 36 | 100 | 100 |
| 42 | 100 | 100 |

Experiment 5

Into a deep Petri dish (diameter of 9 cm), about 250 ml. of each dispersion of each active ingredient having concentration of 100 ppb was charged and striped mosquitos in 3rd instar were put and the Petri dish was covered and kept in a constant temperature bath at 28° C. with light. After 10 days, the mortal larvae were measured and the mortality rates were calculated by the equation of Experiment 1. The results are shown in Table 6.

TABLE 6-1

| Active ingredient | Mortality rate (%) | Active ingredient | Mortality rate (%) |
|---|---|---|---|
| Comp. 31 | 100 | Comp. 36 | 100 |
| 32 | 100 | 37 | 100 |
| 33 | 100 | 38 | 100 |
| 34 | 100 | 42 | 100 |

TABLE 6-1-continued

| Active ingredient | Mortality rate (%) | Active ingredient | Mortality rate (%) |
|---|---|---|---|
| 35 | 100 | | |

Composition 1

| Active ingredient | 20 wt. parts |
|---|---|
| N,N-dimethylformamide | 70 wt. parts |
| Polyoxyethylenealkylphenyl ether | 10 wt. parts |

The components were uniformly blended to dissolve the active ingredient to prepare an emulsifiable concentrate.

Composition 2

| Active ingredient | 5 wt. parts |
|---|---|
| Talc | 95 wt. parts |

The mixture was pulverized to uniformly mix them to prepare a dust.

Composition 3

| Active ingredient | 50 wt. parts |
|---|---|
| Fine silica | 15 wt. parts |
| Fine clay | 25 wt. parts |
| Sodium naphthalenesulfonate-formaldehyde condensate | 2 wt. parts |
| Dialkylsulfosuccinate | 3 "parts |
| Polyoxyethylenealkylaryl ether sulfate | 5 wt. parts |

The mixture was pulverized to uniformly mix them to prepare a wettable powder.

We claim

1. N-benzoyl N'-pyridyloxy phenyl ureas having the formula

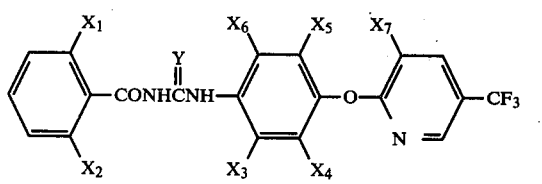

wherein $X_1$ represents a hydrogen or halogen atom or methyl, trifluoromethyl or nitro group; $X_2$ represents a hydrogen or halogen atom; $X_3$, $X_4$, $X_5$ and $X_6$ respectively represent a hydrogen or halogen atom or a $C_1$–$C_4$ alkyl group, a $C_1$–$C_4$ alkoxy group, a $C_1$–$C_4$ alkylcarbonyl group, a $C_1$–$C_4$ alkoxycarbonyl group or nitro group; when $X_3$ and $X_6$ are both hydrogen atoms, at least one of $X_4$ and $X_5$ is a $C_1$–$C_4$ alkyl group, a $C_1$–$C_4$ alkoxy group, a $C_1$–$C_4$ alkylcarbonyl group, or a $C_1$–$C_4$ alkoxycarbonyl group; and $X_7$ represents a hydrogen or halogen atom; and Y represents oxygen or sulfur atom.

2. N-benzoyl N'-pyridyloxy phenyl ureas having the formula

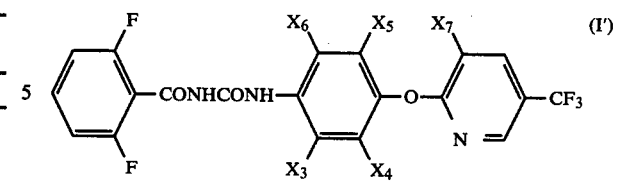

wherein $X_3$, $X_4$, $X_5$ and $X_6$ respectively represent a hydrogen or halogen atom or a $C_1$–$C_4$ alkyl group, A $C_1$–$C_4$ alkoxy group, a $C_1$–$C_4$ alkylcarbonyl group, a $C_1$–$C_4$ alkoxycarbonyl group or nitro group and when $X_3$ and $X_6$ are both hydrogen atoms, at least one of $X_4$ and $X_5$ is a $C_1$–$C_4$ alkyl group, and $X_7$ represents a hydrogen or halogen atom.

3. N-benzoyl N'-pyridyloxy phenyl ureas having the formula

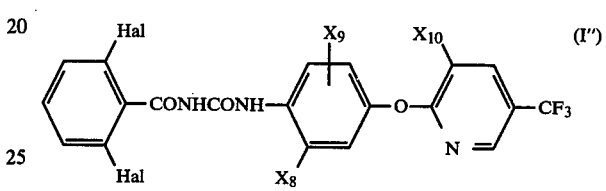

wherein Hal represents a halogen atom; $X_8$ represents a halogen atom, a $C_1$–$C_4$ alkyl group or a $C_1$–$C_4$ alkoxy group; $X_9$ represents a hydrogen or halogen atom or a $C_1$–$C_4$ alkyl group; and $X_{10}$ represents a hydrogen or halogen atom.

4. N-benzoyl N'-pyridyloxy phenyl ureas having the formula

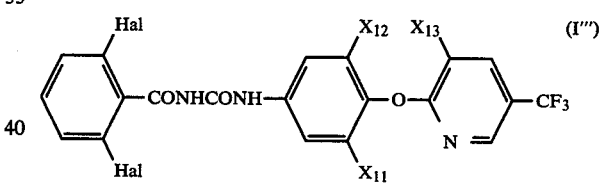

wherein Hal represents a halogen atom; $X_{11}$ represents a $C_1$–$C_4$ alkyl group; $X_{12}$ represents a hydrogen atom or a $C_1$–$C_4$ alkyl group; and $X_{13}$ represents a hydrogen or halogen atom.

5. N-2,6-difluorobenzoyl N'[A-4-(3-halo-5-trifluoromethyl-2-pyridyloxy)phenyl]ureas wherein A represents 2-chloro, 2,5-dichloro, 2-methyl, 2,5-dimethyl or 3-methyl group.

6. An insecticidal composition which comprises an N-benzoyl N'-pyridyloxy phenyl urea having the formula (I) according to claim 1 as an active ingredient, together with an inert carrier.

7. An insecticidal composition which comprises an N-benzoyl N'-pyridyloxy phenyl urea having the formula (I') according to claim 2 as an active ingredient, together with an inert carrier.

8. An insecticidal composition which comprises an N-benzoyl N'-pyridyloxy phenyl urea having the formula (I'') according to claim 3 as an active ingredient, together with an inert carrier.

9. An insecticidal composition which comprises an N-benzoyl N'-pyridyloxy phenyl urea having the formula (I''') according to claim 4 as an active ingredient, together with an inert carrier.

* * * * *